United States Patent
Callahan et al.

(10) Patent No.: US 6,855,521 B2
(45) Date of Patent: Feb. 15, 2005

(54) SEROTYPE AND DENGUE GROUP SPECIFIC FLUROGENIC PROBE BASED PCR (TAQMAN) ASSAYS AGAINST THE RESPECTIVE C AND NS5 GENOMIC AND 3' NON-CODING REGIONS OF DENGUE VIRUS

(75) Inventors: Johnny Dale Callahan, Severn, MD (US); Joseph John Temenak, Takoma Park, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/726,345

(22) Filed: Dec. 1, 2000

(65) Prior Publication Data

US 2004/0126387 A1 Jul. 1, 2004

Related U.S. Application Data

(60) Provisional application No. 60/168,184, filed on Dec. 1, 1999.

(51) Int. Cl.[7] ................................................. C12P 19/34
(52) U.S. Cl. ........................... 435/91.2; 435/6; 536/22.1
(58) Field of Search .............................. 435/91.2, 5, 6, 435/22.1; 536/22.1

(56) References Cited

PUBLICATIONS

Laue et al, Detection of Dengue virus RNA in patients after primary or secondary dengue infection using the TaqMan automated amplification system, Journal of Clinical Microbiology, 1999, vol. 37(8), pp. 2543–2547.*

* cited by examiner

*Primary Examiner*—James Ketter
*Assistant Examiner*—Tara L. Garvey
(74) *Attorney, Agent, or Firm*—Joseph K. Hemby, Jr.; Philip E. Ketner

(57) ABSTRACT

Five fluorogenic probe hydrolysis reverse transcriptase-polymerase chain reaction (RT-PCR) (TaqMan™) assays are described for serotype-specific detection of dengue 1-4 and group-specific detection of dengue viruses. Type- and group-specific oligonucleotide primers and fluorogenic probes were designed against conserved regions of the dengue genome. The invention provides TaqMan PCR assays, which are rapid, sensitive, and specific screening and serotyping tools for the epidemiological study of dengue infections.

5 Claims, No Drawings

SEQUENCE LISTING

<160> NUMBER OF SEQ ID NOS: 16

<210> SEQ ID NO 1
<211> LENGTH: 21
<212> TYPE: DNA
<213> ORGANISM: Dengue virus

<400> SEQUENCE: 1
gacaccacac cctttggaca a                                    21

<210> SEQ ID NO 2
<211> LENGTH: 20
<212> TYPE: DNA
<213> ORGANISM: Dengue virus

<400> SEQUENCE: 2
cacctggctg tcacctccat                                      20

<210> SEQ ID NO 3
<211> LENGTH: 31

```
<212> TYPE: DNA
<213> ORGANISM: Dengue virus

<400> SEQUENCE: 3
agagggtgtt taaagagaaa gttgacacgc g                              31

<210> SEQ ID NO 4
<211> LENGTH: 19
<212> TYPE: DNA
<213> ORGANISM: Dengue virus

<400> SEQUENCE: 4
ccgcgtgtcg actgtacaa                                            19

<210> SEQ ID NO 5
<211> LENGTH: 21
<212> TYPE: DNA
<213> ORGANISM: Dengue virus

<400> SEQUENCE: 5
cagggccatg aacagtttta a                                         21

<210> SEQ ID NO 6
<211> LENGTH: 24
<212> TYPE: DNA
<213> ORGANISM: Dengue virus

<400> SEQUENCE: 6
ttggaatgct gcagggacg agga                                       24

<210> SEQ ID NO 7
<211> LENGTH: 20
<212> TYPE: DNA
<213> ORGANISM: Dengue virus

<400> SEQUENCE: 7
gggaaaaccg tctatcaata                                           20

<210> SEQ ID NO 8
<211> LENGTH: 21
<212> TYPE: DNA
<213> ORGANISM: Dengue virus

<400> SEQUENCE: 8
cgccataacc aatttcattg g                                         21

<210> SEQ ID NO 9
<211> LENGTH: 29
<212> TYPE: DNA
<213> ORGANISM: Dengue virus

<400> SEQUENCE: 9
cacagttggc gaagagattc tcaacagga                                 29

<210> SEQ ID NO 10
<211> LENGTH: 21
<212> TYPE: DNA
<213> ORGANISM: Dengue virus

<400> SEQUENCE: 10
tgaagagatt ctcaaccgga c                                         21

<210> SEQ ID NO 11
```

-continued

```
<211> LENGTH: 19
<212> TYPE: DNA
<213> ORGANISM: Dengue virus

<400> SEQUENCE: 11
aatccctgct gttggtggg                                                    19

<210> SEQ ID NO 12
<211> LENGTH: 27
<212> TYPE: DNA
<213> ORGANISM: Dengue virus

<400> SEQUENCE: 12
tcatcacgtt tttgcgagtc ctttcca                                           27

<210> SEQ ID NO 13
<211> LENGTH: 25
<212> TYPE: DNA
<213> ORGANISM: Dengue virus

<400> SEQUENCE: 13
aaggactaga ggttakagga gaccc                                             25

<210> SEQ ID NO 14
<211> LENGTH: 23
<212> TYPE: DNA
<213> ORGANISM: Dengue virus

<400> SEQUENCE: 14
ggcgytctgt gcctggawtg atg                                               23

<210> SEQ ID NO 15
<211> LENGTH: 27
<212> TYPE: DNA
<213> ORGANISM: Dengue virus

<400> SEQUENCE: 15
aacagcatat tgacgctggg agagacc                                           27

<210> SEQ ID NO 16
<211> LENGTH: 27
<212> TYPE: DNA
<213> ORGANISM: Dengue virus

<400> SEQUENCE: 16
aacagcatat tgacgctggg aaagacc                                           27
```

SEROTYPE AND DENGUE GROUP SPECIFIC FLUROGENIC PROBE BASED PCR (TAQMAN) ASSAYS AGAINST THE RESPECTIVE C AND NS5 GENOMIC AND 3' NON-CODING REGIONS OF DENGUE VIRUS

RELATED APPLICATIONS

This application claims the benefit of Provisional Application Ser. No. 60/168,184, filed on Dec. 1, 1999.

BACKGROUND OF THE INVENTION

1. Field of the Invention

This invention relates to detection assays useful in providing quantitative measurements of dengue virus as well as providing qualitative detection of any dengue serotype virus in research samples.

2. Description of the Prior Art

Dengue viruses are a major public health concern with serious medical and economic consequences and are currently considered the most important arthropod disease affecting humans in terms of morbidity and mortality. (1,2) Dengue fever is endemic in most tropical and subtropical areas worldwide and several hundred thousand dengue hemorrhagic fever cases are reported to occur annually. (3) Due to the vast expansion of air travelling, new dengue virus strains may introduced into a susceptible population in the tropics. Also tourists with dengue fever are now frequently seen in areas where dengue fever is not endemic and where physicians are not familiar with the disease. As symptoms of dengue fever are usually non-specific, a reliable diagnosis is difficult to obtain unless virological techniques are included. (3)

Both dengue virus-specific immunoglobulin G (IgG) and IgM antibodies are usually found in the sera from patients with acute primary infections, while the IgM response may be low or sometimes even absent in secondary dengue fever. (3) However, a strong antibody cross-reactivity exists among the flavivirus family. Therefore, the antibody response may be difficult to interpret with regard to an acute dengue fever, if other flavivirus infections cannot be excluded by clinical, laboratory, or epidemiological means. (3)

Previous methods of quantitating dengue viremia involved the isolation of virus from samples using tissue culture, IFA (immunofluorescent antibody), and plaque titer methods. These classical methods are considered the gold standard; however, these methods are tedious, slow, and often difficult to standardize, and require specialized expertise. The total turn-around time is often two to three weeks and the isolation rates and sensitivity are low. Laue et al., reports the detection of dengue virus RNA by reverse transcriptase PCR (RT-PCR) in human serum or plasma samples is highly indicative of acute dengue fever. (3) Moreover this method is able to identify the dengue virus serotype by demonstrating defined sequence homologies in the viral genomic RNA. Unfortunately, the technique of RT-PCR is handicapped both by time-consuming nested amplification protocols and by false positive reactions which may in part be due to the contamination of dengue virus DNA in the laboratory. (3)

Laue et al. sought to overcome this problem by applying a fully automated amplification protocol which sensitively detects the four serotypes but avoids DNA contamination. The protocol uses the TaqMan priniciple by monitoring a fluorescent signal which tracks the increase in dengue virus-specific DNA during amplification in tightly sealed test tubes. This protocol was viewed as being a simple, highly specific and sensitive test since the test tubes no longer needed to be opened, as in previous methods, to quantitate the PCR product. (3)

Figuerido et al. teach a simplified RT-PCR for identification of dengue virus types 1 and 2 in a single reaction vessel, carried out in a 1/10 dilution of virus in distilled water or in a detergent mixture containing Nonidet P40. The reaction mixture included 50 pmol of specific primers amplifying a 482 base pair sequence for dengue type 1 and 210 base pair sequence for dengue type 2. In other assays, dengue virus consensus primers having maximum sequence similarity to the four serotypes was used which amplified a 511 base pair sequence. The reaction mixture contained 0.1 mM of the four deoxynucleoside triphosphates, 7.5 U of reverse transcriptase, 1 U of thermostable Taq DNA polymerase. The mixture was incubated followed by 2-step PCR amplification with slow temperature increment. Specific DNA amplification was observed with all the Brazilian dengue strains by using dengue virus consensus primers. This technique was found to be less laborious, faster, with reduced risk of contamination.

SUMMARY OF THE INVENTION

Accordingly, an object of this invention is an assay which provides qualitative detection of any dengue serotype in research samples.

Another object of this invention is an assay which provides quantitative measurements of dengue virus in research samples.

Another object of this invention is specific primers and probes which amplify and hybridize with the C genomic region of dengue virus serotype 1 and NS5 target genomic regions of dengue viruses, types 2, 3, and 4.

Yet another object of this invention is specific primers and probes which amplify and hybridize with the 3' non-coding regions of all four dengue virus serotypes.

These and additional objects of the invention are accomplished by amplifying the dengue virus C and NS5 genomic regions of a research sample using specific primers and then hybridizing the sample with specific probes for quantitative and qualititative detection.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements. The representations in each of the figures is diagrammatic and no attempt is made to indicate actual scales or precise ratios. Proportional relationships are shown as approximations.

DESCRIPTION OF THE PREFERRED EMBODIMENTS

Five fluorogenic probe hydrolysis reverse transcriptase-polymerase chain reaction (RT-PCR) (TaqMan™) assays were developed for serotype-specific detection of dengue 1-4 and group-specific detection of dengue viruses. Type- and group-specific oligonucleotide primers and fluorogenic probes were designed against conserved regions of the dengue genome. The PCR assay consisted of a 30 minute RT step, linked to a 45 cycle PCR at 95° and 60° C. Assays were validated against 100 viremic human sera received from two overseas US Military laboratories. The Taqman assays were tested in parallel against the "gold standard", virus isolation using C6/36 cells followed by immunofluorescence assay with serotype-specific monoclonal antibodies., . Virus titers in sera were determined by a direct plaque assay in Vero cells. Among the 100 samples received from overseas, 56 samples were positive by re-isolation in C6/36. The type-specific TaqMan PCR assay detected 51 of 56 confirmed positive samples for a sensitivity of 91.1% while group-specific assay detected 55 of 56 for a sensitivity of 98.2%. The TaqMan type-specific assay also detected viral RNA in 30 samples and group-specific assay detected 32 of the 44 samples that were re-isolation negative. The TaqMan PCR had a specificity of 100% based on results of testing the 21 normal sera. These results indicated that these TaqMan PCR assays could be rapid, sensitive, and specific screening and serotyping tools for the epidemiological study of dengue infections.

Having described the invention, the following examples are given to illustrate specific applications of the invention including the best mode now known to perform the invention. These specific examples are not intended to limit the scope of the invention described in this application.

TaqMan Procedures

During TaqMan amplification an internal probe hybridizes within the region of specific amplification. This internal probe is labeled with two different dyes. When the two dyes are in close proximity, as is the case in intact oligonucleotide probe, one of the dyes (TAMRA[N,N,N',N'-tetramethyl-6-carboxyrhodamine])acts as a quencher for the second fluorescent dye (FAM [5-carboxyfluorescein) by absorbing at the FAM emission spectra. The 5' exonuclease activity of Taq polymerase will degrade an internally hybridizing probe during the course of PCR. The degradation of the probe leads to the separation of these two dyes in solution, with a subsequent increase in the level of fluorescence in the reaction mixture. The amount of fluorescence measured in a sample is proportional to the amount of specific PCR product generated. The amplified material is discarded without opening the test tubes. Thus, the contamination of the samples by amplified DNA can be completely avoided.

Adaptation of the Dengue RT-PCR to TaqMan Conditions.

In contrast to other PCR techniques the TaqMan system makes use of a fluorescence-labeled probe that has to be digested by the nuclease activity of the polymerase to monitor the amplification process. (3) For the digestion an almost complete hybridization of the probe to the target DNA is essential. Therefore, a highly conserved region of the dengue virus genome had to be chosen to allow optimum annealing not only of the primers but also of the labeled probe as discussed in Laue et al. (3)

Sequences

Multiple flaviviral sequences were down loaded from the National Center for Biological Information (NCBI) website. Multiple sequences were aligned utilizing the MacIntosh computer and the "DNA-Star" programs Edit Seq and MegAlign as shown in Tables 1–5. A list of the viral strains utilized for sequence alignments are found in Table 6.

Primers/Probes

There are certain regions within the flaviviral genome which are more highly conserved than others. Primers and probes sets were selected within these highly conserved regions of the dengue genome. At first, the C region was used as the target for all of the serotype specific assays. However, in the end, the dengue 1 assay did not reach the level of sensitivity of the other assays. Eventually, a new more sensitive dengue virus type 1 assay was re-designed using the NS5 region as a target. The dengue group assay was designed against a target found in the 3' non-coding region.

Primers were designed to have $T_m$ of 60° C.+/−1° C. using several methods, including the "primer express" and "net primer" program. Methods used to calculate $T_m$ vary widely, so it is important to test the melting point empirically. Probes were designed to have a $T_m$ of 70° C.+/−1° C. and design characteristics recommended by Perkin Elmer, Inc., such as % GC content, $T_m$ length, etc., were considered and incorporated. Primers and probes were ordered on the smallest scale available so that each act could be evaluated before a large-scale order was placed. Probe and primer design are shown in Table 7.

Stocks Used to Validate the Assay.

Dengue 1—PRNT Stock Virus batch #1, West Pack, Walter Reed Army Institute of Research (WRAIR) Lot 0068, $5.6 \times 10^5$ PFU/ml.

PRNT Stock Virus batch #1, West Pack, Walter Reed Army Institute of Research (WRAIR) Lot 0068, $3.8 \times 10^5$ PFU/ml.

HAW VR-71, ATCC, $6.5 \times 10^4$ PFU/ml

Dengue 2 NGC-ATCC, SMB-1 Navy Medical Research Institute Detachment (NAMRID)-Lima, $1.6 \times 10^7$ PFU/ml PRNT Stock Virus batch #1, West Pack, Walter Reed Army Institute of Research (WRAIR) Lot, $6.0 \times 10^6$ PFU/ml.

PRNT Stock Virus batch #2, West Pack, Walter Reed Army Institute of Research (WRAIR) Lot, $1.3 \times 10^5$ PFU/ml.

Dengue 3 PRNT Stock Virus batch #1, West Pack, Walter Reed Army Institute of Research (WRAIR) Lot CH53489, $6.0 \times 10^6$ PFU/ml.

Den-3 SMB-1, H-87 ATCC, Navy Medical Research Institute Detachment (NAMRID)-Lima, $6.0 \times 10^4$ PFU/ml.

Dengue 4 PRNT Stock Virus batch #1, West Pack, Walter Reed Army Institute of Research (WRAIR), $1.5 \times 10^6$ PFU/ml.

Japanese Encephalitis—ATCC Vaccine Strain, Vero-1, C6/36-1, $1.0 \times 10^6$ PFU/ml.

Yellow Fever—ATCC Vaccine Strain, 17D, Vero-1, C6/36-1, $1.25 \times 10^5$ PFU/ml.

All stocks were QC tested by IFA and then ultimately by PCR using gels and the TaqMan assays. QC is documented in the green TaqMan notebook #1. RNA was extracted from test samples using the Qiagen QIAamp viral RNA kit. RNA was then aliquoted and stored at −20° C. Ten-fold (log) dilutions were prepared of each dengue RNA extract using 1×TE as a diluent.

EXAMPLE 1

Assay Evaluation

Using the Perkin Elmer 7700 Instrument, assay specificity was evaluated by testing seroptype specific probe and primer sets against specificity panels that included dengue-1, 2, 3, 4, Japanese Encephalitis, and Yellow Fever Viruses. In the TaqMan system, direct detection of specific PCR products was determined by monitoring the increase in fluorescence of dye-labeled oligonucleotide probe.

The PCR assay consisted of a 30 minute RT step (60° C.), linked to a 15 second melting step (95° C.), and 45 cycles of PCR at temperatures based o the calculated $T_m$ of the primers used (95 ° C. and 60° C.). Primers and probe sets were used to test panels containing extracted viral RNA from several strains each of dengue 1, 2, 3, and 4, and other flaviviruses including Japanese encephalitis, and yellow fever.

No cross-reactivity was observed when each of the dengue serotype specific and group specific primer sets was tested against the viral panels. Sensitivity experiments indicate a range of linearity to at least one log below that of the gold standard plaque titer assay, or 0.1–1.0 plaque forming units (PFU) per volume tested. Assay characteristics are indicated in Table 2.

Preliminary results appear promising and highlight the potential for the dengue TaqMan assay as a tool for the epidemiological and diagnostic investigation of dengue virus.

Febrile illness from what is thought to have been dengue fever has been recognized as a clinical entity for more than 200 years.[1,2] During the past decade, dengue has reemerged at an alarming rate and is considered the most important arbovirus in terms of morbidity, mortality and economic cost with an estimated 100 million dengue virus infections occurring annually.[2,3]

The disease is caused by four serologically related enveloped RNA viruses of the family Flaviviridae of which yellow fever is the type species. The infection is transmitted through the bite of infected mosquitoes and occurs in epidemic and endemic cycles throughout tropical and sub-tropical regions of the world. Dengue infection produces a spectrum of illness, from dengue fever (DF) a flue-like temporarily incapacitating illness, to fulminating syndromes known as dengue hemorrhagic fever (DHF), or dengue shock syndrome (DSS).[4] Primary infection with dengue usually results in a febrile, self-limiting disease; however, secondary infection may result in severe complications such as dengue shock syndrome (DSS) or dengue hemorrhagic fever (DHF). Patients diagnosed with dengue in endemic areas such as South East Asia generally have secondary infection, whereas patients in non-endemic areas are usually diagnosed with primary infection. Characteristic antibody responses to the disease enable serological diagnosis and differentiation between primary and secondary dengue. There is no cure for dengue and treatment is limited to supportive therapies.[5,6] Classical methods for identification of dengue infection include the collection of acute phase sera for viral isolation and identification, followed by collection of convalescent sera for antibody seroconversion studies. Isolation of virus from clinical and field samples is often difficult and frequently unsuccessful even when the appropriate sample is collected at the appropriate time.[7] Isolation success is highly dependent on proper sample collection during the acute phase of the illness, proper shipment, processing, and storage of the sample for laboratory testing. Further confounders are the high level of expertise required for laboratory isolation and identification.[7]

Recent advances in the molecular biology and especially nucleotide sequencing of arthropod borne viruses have enabled comparisons to be made of sequences representing numerous flaviviruses including dengue.[3,4] Sequence alignments have become a powerful tool enabling the design of very specific and sensitive assays for the detection of dengue viral RNA. By aligning multiple sequences representing the four dengue serotypes, it is now possible to design highly specific serotype- and group-specific assays for the dengue viruses. In this study we sought to develop rapid, sensitive, and specific fluorogenic probe based RT-PCR assays to screen and serotype dengue virus infection from human or culture samples.

Methods

Sequence selection and alignment. Dengue nucleotide sequences were retrieved from Genbank and aligned using the Clustal X (1.8) sequence alignment software[5]. Separate alignments were prepared for each of the dengue serotype and group assays using multiple dengue strains (Tables 1 and 2). The dengue 1 target sequence is located within the non-structural protein 5 (NS5) genomic region, the dengue 2, 3, and 4 targets are within the capsid (C) region. Assay target regions were first identified by visual inspection of sequence alignments, then refined by using primer design software[ref] that enables prediction of oligonucluotide melting temperatures, G+C content, dimerization, cross-linking, and secondary structure potential. Primer and probe design characteristics recommended by Perkin Elmer (Foster City, Calif.) were considered and utilized. Table 1 lists the sequences used to prepare serotype specific alignments.

Table 1. Dengue Sequences Aligned to Design Serotype Specific Assays

The design of the dengue group assay required a different approach due to the lack of a sequence homology among the four serotypes of sufficient length to serve as an assay target. However, an alignment of the 3'-untranslated region (3'-UTR) of the sequences listed in table 2, revealed a relatively homologous region near the terminal end of the genome. To overcome mismatches encountered in the sequence alignment, a multiplex format based on a single universal primer set and two probes of slightly different sequence was used. The two probes were of the same length (27 base pairs), and each is labeled with a 3' TAMRA quencher molecule. The probes differ in sequence and thus specificity, the first is labeled with a 6-FAM fluorochrome and has specificity for dengue 1 and 3. The second probe has a 5' MAX fluorochrome, and a single base substitution (G to A, position 22), and is specific for dengue 2 and 4.

The fluorescence of the MAX fluorochrome is detected using the PE 7700 instrument (Perkin Elmer, PE Biosystems, Foster City, Calif.) set to the JOE filter. The multiplex assay specifically targets the 3' non-coding region of the dengue genome and is designed to detect all members of the dengue group. Table 2 lists the sequences used for the 3'-UTR alignment.

Table 2. Dengue Sequences Aligned to Design Group Specific Assays (3'-UTR).

PCR reaction conditions. The EZ-RT-PCR® reagent kits from Perkin Elmer were used to prepare mastermix according to manufacturers recommendations. Final PCR reaction conditions for a 50:1 reaction volume using 5:1 of template were; $Mn(OAc)_2$ 3 mM, KCL 115 mM, primers 0.3: M, probe 0.15: M, dATP/CTP/GTP 0.1 mM, dUTP 0.2 mM, rTth DNA polymerase 0.1 U/ul, and BSA 0.1 ug/ul in a 5× buffer (250 mM Bicine, 575 mM KOAc, 0.05 mM EDTA). The RT-PCR assay consisted of a 30 minute RT step at 60° C., linked to a 45 cycle PCR (95° C.×15 sec, and 60° C.×60 sec).

Development and optimization. The assay was evaluated and optimized against RNA extracted from a panel of stock viruses from the collection maintained at the Naval Medical Research Center, Silver Spring, Md. (Table 3). RNA was extracted from stock virus using the QIAGEN (Valencia, Calif.), QIAamp Viral RNA Mini Kit following the manufacturers directions and stored at −70° C.

Table 3. Stocks Used to Develop the Assay.

Human sera. A total of 100 dengue virus positive human serum samples were received from staff at the US Naval Medical Research Unit 2 (NAMRU 2), Jakarta, Indonesia and the US Naval Medical Research Center Detachment (NMRCD), Lima, Peru and used for evaluation of the NASBA technique. All of these samples were collected from dengue fever patients, including 47 from Indonesia and 53 from Peru. Dengue viruses were isolated from these samples at the NAMRU 2 and NMRCD laboratories in Aedes albopictus C6/36 cell cultures as described in the following section. Among these 100 samples, 53 were positive for dengue-1, 15 for dengue-2, 21 for dengue-3 and 11 samples were positive for dengue-4. A total of 21 normal human serum samples were also collected from healthy donors from U.S.A. and used as negative controls. Serum samples were thawed and tested simultaneously in C6/36 cells and by the TaqMan assays in a randomized, blinded fashion to the viral isolation results obtained at NMRCD and NAMRU 2. Nucleic acid was isolated from human serum samples using the method of Boom et al. (1990). Typically, this procedure utilized 100 μl of plasma or serum as the starting input material. Final nucleic acid extracts were obtained in a total volume of 50 μl.

Viral isolation and immunofluorescence assay. The serum samples were diluted 1:10 in culture medium and inoculated to *Aedes albopictus* mosquito cell line, C6/36, for viral isolation as described previously (Tesh, 1979). Basically, the cell cultures were incubated for 7 days at 28° C. after 1 h absorption period at 28° C. Cells were harvested after 7 days for immunofluorescence assay as described (Wu et al., 2000). Cells were reacted with serotype-specific monoclonal antibodies and fluorescein-isothiocyanate (FITC)-conjugated goat anti-mouse antibody was used as the detector.

Plaque assay in Vero cells. The titers of dengue virus in human serum samples were determined by inoculating samples at 1:5, 1:10 and 1:100 dilutions in culture medium into Vero cells and assayed 7 days later as described (Eckels et al., 1976).

Dengue viruses and negative control viruses. All four dengue virus serotypes were prepared in Vero cells as virus seed stocks and virus titers were determined by the plaque assay. These viruses were used to spike the normal human serum to determine the detection limits of TaqMan and to develop the assay. Other flaviviruses such as yellow fever virus (17D, vaccine strain) and Japanese encephalitis virus (SA14-14-2, live attenuated vaccine strain) were also prepared in Vero cells and used as negative control viruses for cross-reactivity test with the dengue serotype-specific and dengue group-specific TaqMan assays.

Assay evaluation. Using the Perkin Elmer 7700 instrument, direct detection of specific PCR products was detected by monitoring the increase in fluorescence of a dye-labeled oligonucleotide probe. Assay specificity was evaluated by testing serotype specific probe and primer sets against specificity panels that included dengue-1, 2, 3, 4, Japanese Encephalitis, and Yellow Fever Viruses.

The sensitivity of each assay was estimated in two ways, by testing log dilutions of dengue serotype stock viruses of known plaque titer (PFU/ml), and by direct comparison of TaqMan results to human viremic samples simultaneously tested by classical virological methods as described previously.

Dengue viral RNA extracted from stock virus cultures (Table 3) were evaluated by testing log dilutions or RNA in 1×Tris-EDTA (1×-TE) of each specific target. Standard curves were evaluated to determine the lowest log dilution consistently yielding linear results. Standard curves were accepted if the correlation coefficient was >0.900.

The extracted human serum samples were tested using the 5 dengue TaqMan assays in parallel with the routine methods. Results of standard virological and TaqMan methods were then compared.

Results

Each of the dengue serotype assays specifically detected the target virus among the members of the two panels of dengue viral RNA derived from cell culture stocks (Table 3) and human serum samples. Cross reactivity was not observed among any of the four dengue serotype assays. The dengue group assay also successfully detected all dengue viruses in the two panels. All five assays failed to detect Japanese Encephalitis and yellow fever vaccine strains. These results indicate 100% specificity for all assays.

Sensitivity experiments conducted on log dilutions of RNA extracted from dengue stock viruses indicate a range of linearity equal to or beyond the gold standard plaque titer assay, or 0.1–1.0 plaque forming units (PFU) per volume (0.1 ml) tested. Assay characteristics such as sensitivity, specificity, and dynamic range are listed in table 4.

To evaluate TaqMan assays for the detection of dengue viral RNA, we tested 100 dengue virus isolation positive sera collected from dengue patients from overseas and 21 normal human sera from U.S.A. All these samples were thawed and re-isolated for dengue virus by C6/36 cells at the same time when aliquots were lysed by the lysis buffer for TaqMan assay. Among the 100 viremic serum samples received from overseas, 56 samples were confirmed positive and 44 samples were negative by re-isolation in C6/36 cells in our laboratory (Table 2). Based on the 56 re-isolation positive samples, serotype-specific TaqMan assays detected 51 of 56 and group-specific assay detected 55 of 56 for a sensitivity of 91.1% and 98.2%, respectively. Serotype-specific TaqMan assays also detected dengue viral RNA in 30 of the 44 samples that were re-isolation negative in C6/36 cells. Dengue group-specific TaqMan assay detected 32 sera from 44 re-isolation negative sera. TaqMan assays had a specificity of 100% (21/21) based on results of testing the 21 normal human serum samples. The serotype concordance for TaqMan serotype- or group-specific assays with viral isolation method was 100% (51/51 or 55/55, respectively).

In this study, we developed dengue serotype-specific and dengue group-specific TaqMan assays for detecting and typing of dengue viral RNA in the clinical samples. TaqMan assays were shown to be a sensitive and specific method for detecting and typing dengue viral RNA. The detection threshold for the clinical serum samples based on the plaque assay (25 PFU/ml) was equivalent to the detection threshold for the dengue virus spiked-normal serum (1–10 PFU/ml)). These TaqMan assays were also specific to dengue virus as it did not cross-react with other flaviviruses or non-dengue-related virus tested.

The invention provides a dengue TaqMan assay as a rapid, specific, and sensitive tool for the epidemiological and diagnostic investigation of dengue virus.

In conclusion, rapid TaqMan assays were developed for the detection of dengue viral RNA in the clinical samples. TaqMan assays provided high sensitivity and specificity compared with the standard viral isolation method. The total assay procedure takes about 5 hours. Therefore, it is much faster than the tissue culture method, which requires about 7-10 days. This study suggests that TaqMan assays may be used for testing acute phase serum samples from patients clinically suspected to have dengue infection and providing the diagnostic results on the same day. This diagnostic assay based on dengue virus detection could guide clinical care during the acute phase of illness.

References

1. Gubler D J: Dengue and Dengue Hemmorrhagic Fever. Clinical Microbiology Reviews. 1998:11(3), 480–496.
2. Gubler D J. Dengue. In: Epidemiology of arthropod-borne viral disease, Monath TPM, editor. Boca Raton (Fla.): CRC Press, 1988:223–60.
3. Trent D W; Manske C L; Fox G E; Chu M C; Kliks S C; Monath T P: The Molecular Epidemiology of Dengue Viruses, Genetic Variation and Microevolution. In: (1989) Applied Virology Research, Vol. 2, Virus Variation and Epidemiology (E. Kurstk, Eds). Plenum, N.Y.
4. Duebel V: The Contributions of Molecular Techniques to the diagnosis of Dengue Infection. In: (1997) Dengue and Dengue Hemorrhagic Fever (eds Gubler D J, and Kuno G.)

5. Aiyar A: The use of CLUSTAL W and CLUSTAL X for multiple sequence alignment. *Methods Mol Biol* 2000;132:221–41 PMID: 10547838, UI: 20015561
6. Kumar S, Tamura K, Nei M: MEGA: Molecular Evolutionary Genetics Analysis software for microcomputers. *Comput Appl Biosci* 1994 April; 10(2):189–91.
7. Diagnostic Procedures for Viral, Rickettsial and Chlamydial Infections. Ed. Schmidt N J; Emmons R W: 6th Edition, 1989, American Public Health association, ISBN 0-87553-155-5.

Wu SL, Grouard-Vogel G, Sun W, Mascola J R, Brachtel E, Putvatana R, Louder M, Filguera L, Marovich M, Wong H K, Blauvelt A, Murphy G S, Robb M L, Innis B L, Birx D L, Hayes C G, Frankel S S. Human skin Langerhans cells are targets in transmission of dengue virus infection. Nature Medicine 2000; 6(7): 816–820.

TABLE 1

Dengue Sequences aligned to design serotype specific assays

| Virus | Genbank # | Strain | Genomic Target |
|---|---|---|---|
| Dengue 1 | AF226686 | FGA/NA d1d | NS5 |
|  | U88535 | West Pac | NS5 |
|  | M87512 | S275/90 | NS5 |
| Dengue 2 | M29095 | New Guinea-C | C |
|  | AF169688 | ThNH81/93 | C |
|  | AF022439 | ThNH-p14/93 | C |
|  | M20558 | DEN2JAM | C |
|  | AF119661 | China isolate 04 | C |
| Dengue 3 | M93130 | H87 | C |
|  | AF008555 | CH53489(D73-1) | C |
|  | AB010990 | Z026, MALAY94-3 | C |
|  | AB010982 | JM086, MALAY93-3 | C |
| Dengue 4 | M14931 | 814669 | C |
|  | S66064 | H241-P | C |

TABLE 2

Dengue Sequences aligned to design group specific assays (3'-UTR).

| Virus | Genbank # | Strain |
|---|---|---|
| Dengue 1 | M87512 | S275/90 |
|  | M87512 | S275/90 |
| Dengue 2 | M29095 | New Guinea-C |
|  | AF100151 | 044 |
|  | AF100465 | Ven2 |
|  | AF100466 | Mara4 |
|  | AF100469 | 0131 |
|  | AF022434 | ThNHp7/93 |
|  | AF022437 | ThNH11/93 |
|  | AF100459 | K0008 |
|  | AF100460 | K0010 |
|  | AF100461 | CO371 |
|  | AF100462 | CO390 |
|  | AF100467 | IQT1797 |
|  | AF100468 | IQT2913 |
|  | AF100463 | CO166 |
|  | AF100464 | CO167 |
|  | AF100146 | 926 |
|  | M20558 | DEN2JAM |
|  | AF204178 | 43 |
|  | AF276619 | FJ-10 |
| Dengue 3 | M93130 | H-87 |
| Dengue 4 | M14931 | unreported |

TABLE 3

Stocks used for assay development.

| Virus | Strain or Lot | Titer |
|---|---|---|
| Dengue 1 | West Pack, WRAIR, Lot 0068 | $5.6 \times 10^5$ PFU/ml. |
| Dengue 1 | West Pack, WRAIR, Lot 0068 | $3.8 \times 10^5$ PFU/ml |
| Dengue 1 | HAW VR-71, ATCC | $6.5 \times 10^4$ PFU/ml |
| Dengue 1 | Philippines Strain -029 | $5.5 \times 10^4$ PFU/ml |
| Dengue 2 | NGC-ATCC, SMB-1 (NAMRID-Lima) | $1.6 \times 10^7$ PFU/ml |
| Dengue 2 | PRNT-Stock Virus, batch #1, WRAIR | $6.0 \times 10^6$ PFU/ml |
| Dengue 2 | PRNT-Stock Virus, batch #2, WRAIR | $1.3 \times 10^5$ PFU/ml |
| Dengue 3 | PRNT-Stock Virus, batch #1, WRAIR (Lot CH53489 | $6.0 \times 10^6$ PFU/ml |
| Dengue 3 | SMB-1, H-87 ATCC, (NAMRID Lima) | $6.5 \times 10^4$ PFU/ml |
| Dengue 4 | PRNT-Stock Virus, batch #1, WRAIR | $1.5 \times 10^6$ PFU/ml |
| Japanese Encephalitis | ATCC Vaccine Strain | $1.0 \times 10^6$ PFU/ml |
| Yellow Fever | ATCC Vaccine Strain, 17D | $1.25 \times 10^5$ PFU/ml |

TABLE 4

Assay Characteristics

| Assay | Target | Detection limit (PFU/0.1 ml) | Std Curve Correlation Coefficient | Cross-reactivity | Serotype Concordance (%) |
|---|---|---|---|---|---|
| Dengue 1 | Den 1 | 0.3 | 0.900 | Non observed | 100 |
| Dengue 2 | Den 2 | 0.1 | 0.900 | Non observed | 100 |
| Dengue 3 | Den 3 | 1.1 | 0.900 | Non observed | 100 |
| Dengue 4 | Den 4 | 0.1 | 0.900 | Non observed | 100 |
| Den Group | Den 1–4 | 0.1–1.0 | 0.900 | Non observed | 100 |

TABLE 5

Dengue Serotype Specific Probe and Primer design (5'-3')

| Direction | mer | Sequence | Name | Target |
|---|---|---|---|---|
| Forward | 21 | gac acc aca ccc ttt gga caa | DEN-1-1036F | NS5 region |
| Reverse | 20 | cac ctg gct gtc acc tcc at | DEN-1-1143R | NS5 region |
| Probe | 31 | aga ggg tgt tta aag aga aag ttg aca cgc g | DEN-1-1058-T | NS5 region |
| Forward | 16 | ccg cgt gtc gac tgt aca a | DEN-2-159-F | C Region |
| Reverse | 22 | cag ggc cat gaa cag ttt taa | DEN-2-248-R | C Region |
| Probe | 24 | ttg gaa tgc tgc agg gga cga gga | DEN-2-201-T | C Region |
| Forward | 20 | ggg aaa acc gtc tat caa ta | DEN-3-25F | C Region |
| Reverse | 21 | cgc cat aac caa ttt cat tgg | DEN-3-148R | C Region |
| Probe | 29 | cac agt tgg cga aga gat tct caa cag ga | DEN-3-81-T | C Region |
| Forward | 21 | tga aga gat tct caa ccg gac | DEN-4-89F | C Region |
| Reverse | 19 | aat ccc tgc tgt tgg tgg g | DEN-4-195R | C Region |
| Probe | 27 | tca tca cgt ttt tgc gag tcc ttt cca | DEN-4-149-T | C Region |

TABLE 6

Group Specific Dengue Probe and Primer designs. (5'-3")

| Direction | mer | Sequence | Name | Target |
|---|---|---|---|---|
| Forward | 25 | aag gac tag agg tta kag gag acc c | DEN-GR-10616F | 3' non coding region |
| Reverse | 23 | ggc gyt ctg tgc ctg gaw tga tg | DEN-GR-10726R | 3' non coding region |
| Probe 1 | 27 | FAM-aac agc ata ttg acg ctg gga gag acc-TAMRA | DEN-1-3-10655-T | 3' non coding region |
| Probe 2 | 27 | MAX-aac agc ata ttg acg ctg gga aag acc-TAMRA | DEN-2-4-10655-T | 3' non coding region |

TABLE 7

Re-isolation results obtained at NMRC for 100 viremic human sera

| Dengue serotype | No. of positive sera | No. of negative sera |
|---|---|---|
| Dengue-1 | 29 | 24 |
| Dengue-2 | 9 | 6 |
| Dengue-3 | 14 | 7 |
| Dengue-4 | 4 | 7 |
| Total | 56 | 44 |

What is claimed is:

1. A method of detecting the presence of Dengue virus by polymerase chain reaction, said method comprising:
   a) providing the RNA of said Dengue virus or a test sample of RNA suspected of being Dengue virus RNA, RT enzymes, dATPs, dGTPs, dCTPs, dTTPs and buffer containing divalent cations in sufficient quantities so reverse transcription of a cDNA copy occurs,
   b) providing group specific or serotype-specific primers and probes of Dengue in sufficient quantities so amplification of a target sequence of DNA occurs,
   c) detecting the presence of the amplification products of the target sequence of DNA as an indication of the presence of Dengue virus.

2. A method of detecting the presence of Dengue-1 virus by polymerase chain reaction, said method comprising:
   a) providing the RNA of said Dengue-1 virus or a test sample of RNA suspected of being Dengue-1 virus RNA, RT enzymes, dATPs, dGTPs, dCTPs, dTTPs and buffer containing divalent cations in sufficient quantities so reverse transcription of a cDNA copy occurs,
   b) providing serotype-specific primers and a probe for Dengue-1 virus in sufficient quantities so amplification of a target sequence of DNA occurs,
   c) detecting the presence of the amplification products of the target sequence of DNA as an indication of the presence of Dengue-1 virus.

3. A method of detecting the presence of Dengue-2 virus by polymerase chain reaction, said method comprising:
   a) providing the RNA of said Dengue-2 virus or a test sample of RNA suspected of being Dengue-2 virus RNA, RT enzymes, dATPs, dGTPs, dCTPs, dTTPs and buffer containing divalent cations in sufficient quantities so reverse transcription of a cDNA copy occurs, b) providing serotype-specific primers and a probe for Dengue-2 virus in sufficient quantities so amplification of a target sequence of DNA occurs, c) detecting the presence of the amplification products of the target sequence of DNA as an indication of the presence of Dengue-2 virus.

4. A method of detecting the presence of Dengue-3 virus by polymerase chain reaction, said method comprising:

a) providing the RNA of said Dengue-3 virus or a test sample of RNA suspected of being Dengue-3 virus RNA, RT enzymes, dATPs, dGTPs, dCTPs, dTTPs and buffer containing divalent cations in sufficient quantities so reverse transcription of a cDNA copy occurs, b) providing serotype-specific primers and a probe for Dengue-3 virus in sufficient quantities so amplification of a target sequence of DNA occurs, c) detecting the presence of the amplification products of the target sequence of DNA as an indication of the presence of Dengue-3 virus.

5. A method of detecting the presence of Dengue-4 virus by polymerase chain reaction, said method comprising:

a) providing the RNA of said Dengue-4 virus or a test sample of RNA suspected of being Dengue-4 virus RNA, RT enzymes, dATPs, dGTPs, dCTPs, dTTPs and buffer containing divalent cations in sufficient quantities so reverse transcription of a cDNA copy occurs, b) providing serotype-specific primers and a probe for Dengue-4 virus in sufficient quantities so amplification of a target sequence of DNA occurs, c) detecting the presence of the amplification products of the target sequence of DNA as an indication of the presence of Dengue-4 virus.

* * * * *